(12) United States Patent
Bay

(10) Patent No.: US 6,448,398 B1
(45) Date of Patent: Sep. 10, 2002

(54) PROCESS FOR PREPARING ACID AMIDES FROM (SI, GE, OR SN SUBSTITUTED AMINO)-1,3,5-TRIAZINES AND ACID HALIDES

(75) Inventor: William Elliott Bay, Ridgefield, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 08/324,549

(22) Filed: Oct. 18, 1994

(51) Int. Cl.[7] ............... C07D 251/16; C07D 251/18; C07D 251/44
(52) U.S. Cl. ............ 544/181; 544/194; 544/196; 544/200; 544/204; 544/207; 544/212
(58) Field of Search ................ 544/181, 194, 544/196, 200, 204, 207, 212

(56) References Cited

U.S. PATENT DOCUMENTS

| | | |
|---|---|---|
| 3,732,223 A | 5/1973 | Gizycki et al. .......... 260/249.8 |
| 3,919,221 A | 11/1975 | Dazzi ...................... 260/249.5 |
| 4,444,954 A | 4/1984 | Mels et al. ................ 525/124 |
| 4,939,213 A | 7/1990 | Jacobs, III et al. ...... 525/329.9 |
| 5,084,541 A | 1/1992 | Jacobs, III et al. ........... 528/45 |
| 5,288,865 A | 2/1994 | Gupta ..................... 544/200 |

OTHER PUBLICATIONS

Tetrahedron Letters, vol. 28(43), pp 5099–5102, 1987.*
J. Org. Chem., 51, pp 1610–1612, 1986.*
CA(104): 148979, 1985.*
CA(107): 58801, 1986.*
Mironov et al., "Transformations of Compounds having a Si–N–C–X Connecting System a New Method For Obtaining Isocyanates Through The Phosgenation of N–Silyl Substituted Amines", *Zh. Obshch. Khim.* 39(11), pp. 2598–2599 (1969) (Translation).
Chemical Abstracts No. 66300r. vol. 72 p. 328 (1970).
L. Rappaport et al., "S–Triazines and Derivatives," Interscience Publishers Inc. p. 333, (1959).
M.J. Coghlan and B.A. Caley, "Trichloromethyl Carbonate as a Practical Phosgene Source", *Tetrahedron Letters*, vol. 30, No. 16, pp. 2033–2036 (1989).

* cited by examiner

*Primary Examiner*—Yogendra N. Gupta
(74) *Attorney, Agent, or Firm*—James A. Jubinsky; Valerie T. Didamo; Claire M. Schultz

(57) ABSTRACT

A process is disclosed for preparing acid amides, including isocyanate-functional 1,3,5-triazines and isocyanate-based 1,3,5 triazine derivatives, from the reaction of (Si, Ge or Sn substituted amino)-1,3,5 triazines and acid halides.

34 Claims, No Drawings

US 6,448,398 B1

PROCESS FOR PREPARING ACID AMIDES FROM (SI, GE, OR SN SUBSTITUTED AMINO)-1,3,5-TRIAZINES AND ACID HALIDES

BACKGROUND OF THE INVENTION

1. Field of the Invention

This invention relates to the preparation of acid amides by reacting (Si, Ge or Sn substituted amino)-1,3,5-triazines, such as (N-silylated amino)-1,3,5-triazines, with acid halides.

2. Description of Related Art

Various derivatives of amino-1,3,5-triazines are described in the literature for use in a wide variety of fields. Certain of these derivatives, such as alkoxymethyl derivatives of melamine and guanamines, are useful as crosslinkers or reactive modifiers in curable compositions which contain resins having active hydrogen groups. While alkoxymethylated melamines and guanamines provide excellent results in a number of aspects, they also have the disadvantage of releasing formaldehyde as a volatile by-product under curing conditions. It has long been a desire of industry to find acceptable alternatives which do not emit formaldehyde upon cure.

One such alternative which has shown great promise is carbamate and isocyanate functional 1,3,5-triazines disclosed in U.S. Pat. Nos. 4,939,213, 5,084,541, 5,288,865, U.S. application Ser. No. 07/998,313 (filed Dec. 29, 1992), U.S. application Ser. No. 08/061,905 (filed May 13, 1993), U.S. application Ser. No. 08/138,581 (filed Oct. 15, 1993), U.S. application Ser. No. 08/239,009 (filed May 6, 1994), and U.S. application Ser. No. 08/286,835 (filed Aug. 5, 1994), all of which are commonly owned with the present application and all of which are hereby incorporated by reference herein as if fully set forth. The carbamate and isocyanate functional 1,3,5-triazines disclosed in these references have been found to be particularly useful as crosslinkers in coating compositions based upon hydroxy functional resins, with the cured coatings possessing a wide range of desirable properties.

The ability of carbamate and isocyanate functional 1,3,5-triazines to perform as efficient non-formaldehyde emitting crosslinking agents, particularly in curable coating compositions, has initiated intensive research directed towards the discovery of practical and economical processes for their production, a number of which are disclosed in the previously incorporated references. While a number of these processes have shown great promise, certain of them also have some drawbacks including, for example, the required use of expensive starting materials and/or low ultimate yield of the desired products.

In addition to the processes of the aforementioned incorporated references, it has now been surprisingly discovered that acid amides can be prepared with excellent yields by reacting (Si, Ge or Sn substituted amino)-1,3,5-triazines, such as silylated melamine, with acid halides. It has also been discovered that the use of a acid halide selected from the group consisting of oxalyl chloride, phosgene or phosgene analogs provides excellent yields of isocyanate-functional 1,3,5-triazines. The isocyanate-functional 1,3,5-triazines may be further derivatized by contacting the same with a wide variety of well-known isocyanate-reactive materials. For example, these isocyanates may be readily "blocked" (for example, converted to the corresponding carbamate) by adding a blocking agent (such as a hydroxyl compound) to the isocyanate-functional 1,3,5-triazine without isolating it. In addition, the isocyanates may be readily oligomerized by adding a multifunctional isocyanate-reactive compound (for example, a diol or diamine) to the isocyanate-functional 1,3,5-triazine without isolating it.

It should be noted that it is generically known to obtain isocyanates by phosgenation of silylated amines as disclosed in Mironov et al., Zh. Obshchei. Khim. 1969, 39(11), 2598–9 and Chem. Abstracts No. 66300r, Vol.72, 1970, p.328. It is, however, also well known that the amine functionality of amino-1,3,5-triazines, such as melamine, is not equivalent to other types of typical amine functionality. Significantly, melamines are among the least reactive of the "amines" and the most difficult to functionalize, and their behavior cannot normally be correlated to that of other known amines.

For example, most "typical" amines are highly reactive with acid halides. In a publication by E. M. Smolin and L. Rappaport entitled "S-Triazines and Derivatives," Interscience Publishers Inc., New York, page 333 (1959), it is reported that attempts to react an acid halide with the amino group on a 1,3,5-triazine such as melamine were not successful. Further, attempts to functionalize amino-1,3,5-triazine often results in substitution at the nitrogen on the triazine ring. For example, it is known that the reaction of melamine with alkyl halides, such as allyl chloride, results in alkyl substitution at the nitrogen on the triazine ring resulting in isomelamine derivatives.

Indeed, it is reported in U.S. Pat. No. 3,732,223 that the well-known phosgenation of amines fails to produce isocyanate functionality when applied to amino-1,3,5-triazines. In subsequent U.S. Pat. No. 3,919,221, the phosgenation of amino-1,3,5-triazines having one or two unsubstituted amino groups attached to the triazine ring to obtain monoisocyanato and diisocyanato triazines is reported to occur under certain specified conditions. These references do not, however, suggest that (Si, Ge or Sn substituted amino)-1,3,5-triazines can be reacted with acid halides, such as phosgene, to produce acid amides, and particularly isocyanate-functional 1,3,5-triazines, in significant yields.

Surprisingly, a procedure has now been discovered in which acid halides, including phosgene (and phosgene sources) and halogenated formates, can readily and effectively be reacted with (Si, Ge or Sn substituted amino)-1,3,5-triazines to produce a corresponding acid amide, including isocyanate- and carbamate-functional 1,3,5-triazines. Moreover, the isocyanate-functional derivatives can further be readily and effectively reacted with known isocyanate-reactive materials (such as blocking agents) to produce the corresponding isocyanate-based derivatives thereof.

SUMMARY OF THE INVENTION

In accordance with the present invention, there is provided a process for preparing acid amides which, in its overall concept, comprises the step of contacting:

(a) a (Si, Ge or Sn substituted amino)-1,3,5-triazine represented by the formula:

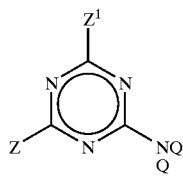

wherein
wherein Z and $Z^1$ are independently selected from the group consisting of hydrogen, a hydrocarbyl, a hydrocarbyloxy, a hydrocarbylthio, a group represented by the formula —N(Q)$_2$, and a group represented by the formula:

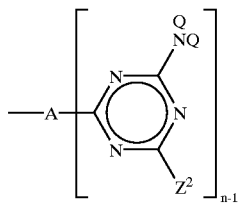

each Q is independently selected from the group consisting of hydrogen, hydrocarbyl, hydrocarbyloxy hydrocarbyl and $M(R^1)_3$, provided that at least one Q group is $M(R^1)_3$,
A is an n-functional anchor,
n is at least 2,
each $Z^2$ is independently selected from the group consisting of hydrogen, a hydrocarbyl, a hydrocarbyloxy, a hydrocarbylthio and a group represented by the formula N(Q)$_2$,
each M is independently selected from the group consisting of silicon, germanium and tin, and
each $R^1$ is independently selected from substituted or unsubstituted alkyl, alkenyl, aryl, aralkyl and alkoxy groups; and (b) an acid halide,
under reaction conditions sufficient to produce a corresponding acid amide derivative.

As indicated above, an acid amide is produced by contacting an acid halide with the (Si, Ge or Sn substituted amino)-1,3,5-triazine. An isocyanate-functional 1,3,5-triazine is produced by employing, for example, phosgene, oxalyl chloride or a phosgene analog as the acid halide. This isocyanate-functional 1,3,5-triazine may be reacted with isocyanate-reactive materials to produce various isocyanate-based derivatives. For example, the isocyanate groups may be blocked by contacting the isocyanate-functional 1,3,5-triazines with known isocyanate blocking agents, such as certain active hydrogen containing compounds. As another example, oligomers of the isocyanate-functional 1,3,5-triazines can be produced by contacting the same with multifunctional isocyanate-reactive materials such as diols and diamines. The phrase "isocyanate and/or isocyanate-based" 1,3,5-triazines, in the context of the present invention, includes triazine derivatives having isocyanate functionality, isocyanate-based functionality, or a mixture of isocyanate and isocyanate-based functionality. For example, when a blocking agent is added in an amount which is less than the molar equivalent of the available isocyanate functionality, then a triazine derivative is produced having both isocyanate and blocked-isocyanate functionality.

If the acid halide employed in the present invention is a hydrocarbyl haloformate, such as an alkyl or aryl haloformate, then the resulting acid amide is a carbamate-functional 1,3,5-triazine. When the process is practiced in this manner, there is no need to add an isocyanate-reactive material as described above to obtain a 1,3,5-triazine derivative having carbamate functionality.

The process of the instant invention can also be practiced by preparing the (Si, Ge or Sn substituted amino)-1,3,5-triazine in situ. This is accomplished by mixing an amino-1,3,5-triazine and a silicon-, germanium- or tin-containing reactive compound, such as for example, chlorotrimethylsilane, along with the acid halide.

The process of this invention is advantageous because no halogenated amino-1,3,5-triazine starting materials are required. Further, the yield of the acid amide product is increased by employing the (Si, Ge or Sn substituted amino)-1,3,5-triazine compound compared to the use of an unsubstituted triazine. Moreover, the (Si, Ge or Sn substituted amino)-1,3,5 triazines, such as N-silylated melamine, can be reacted with, for example, phosgene, followed by reaction of the isocyanate with any one of a wide variety of well-known isocyanate-reactive materials to obtain an isocyanate-based 1,3,5-triazine without handling or isolation of the isocyanate triazine product. Alternatively, the (Si, Ge or Sn substituted amino)-1,3,5-triazine can be reacted with an acid halide, such as an alkyl haloformate, to directly obtain an acid halide having carbamate functionality.

A preferred use of the acid amides, including the isocyanate-functional 1,3,5-triazines and various derivatives thereof is as a crosslinking agent with polyfunctional active hydrogen containing resins such as hydroxy-functional acrylic or polyester resins, for producing curable compositions which have utility in coatings, adhesives, molding and other applications. This and other uses are disclosed in various of the previously incorporated references.

These and other features and advantages of the present invention will be more readily understood by those of ordinary skill in the art from a reading of the following detailed description.

DETAILED DESCRIPTION OF THE PREFERRED EMBODIMENTS

As indicated above, the present invention is a novel process for preparing acid amides by contacting a (Si, Ge or Sn substituted amino)-1,3,5-triazine with an acid halide. The term "Si, Ge or Sn substituted amino" means within the context of this invention that a silicon (Si), germanium (Ge) or tin (Sn)-containing group is bound to the amino group of an amino-1,3,5-triazine through (Si), (Ge) or (Sn). The process is carried out under reaction conditions, such as temperature, pressure and for a sufficient time, to result in the formation of the corresponding acid amide.

The term "acid amide" as employed herein includes the reaction products resulting from the combination of the amine group of a (Si, Ge or Sn substituted amino)-1,3,5-triazine with the non-halide portion of an acid halide. When the acid halide employed is, for example, a halo formate, the resulting acid amide is a carbamate-functional 1,3,5-triazine. On the other hand, if the acid halide employed is phosgene, oxalyl chloride or a phosgene analog, the resulting acid amide is an isocyanate-functional 1,3,5-triazine.

When an isocyanate-reactive material such as a well-known isocyanate blocking agent is added subsequent to the formation of the isocyanate-functional 1,3,5-triazine, there is obtained the corresponding 1,3,5-triazine with isocyanate-based (blocked isocyanate) functionality. More highly functional derivatives of such isocyanate-functional 1,3,5-triazines can also be produced by adding a multifunctional isocyanate-reactive material subsequent to the formation of the isocyanate-functional 1,3,5-triazine.

The (Si, Ge or Sn Substituted Amino)-1,3,5-Triazine Starting Materials

The (Si, Ge or Sn substituted amino)-1,3,5-triazine starting materials, such as tris(trimethylsilyl) melamine, i.e., N,N',N"-tris(trimethylsilyl)-2,4,6-triamino-1,3,5-triazine, and oligomers thereof, can be readily prepared using standard and well known techniques to silylate, germanylate and/or tinylate the amino group(s) of amino-1,3,5-triazines.

The term "(Si, Ge or Sn substituted amino)-1,3,5-triazine" in the context of this invention includes a monomeric 1,3,5-triazine having at least one and preferably at least two Si, Ge or Sn substituted amino groups attached to the triazine ring (Si, Ge or Sn substituted guanamines and melamines), as well as various N-substituted oligomers of 1,3,5-triazines (e.g., dimers, trimers and tetramers) having at least two Si, Ge or Sn substituted amino groups attached to the triazine rings per molecule.

The term "hydrocarbyl" in the context of the present invention, and in the above formula, is a group which contains carbon and hydrogen atoms and includes, for example, alkyl, aryl, aralkyl, alkenyl, and substituted derivatives thereof. Likewise, the term "hydrocarbylene" (as utilized below) refers to a divalent hydrocarbyl such as, for example, alkylene, arylene, alkenylene, and substituted derivatives thereof.

The group A in the above formula is an n-functional anchor which can, for example, be a hydrocarbon residue (e.g., a hydrocarbylene group such as a methylene group), an amino compound residue, NH, N(hydrocarbyl), O, S, $CO_2$, $NHCO_2$, $CO(NH)_2$ and the like. (Si, Ge or Sn substituted amino)-1,3,5-triazines containing this A group are referred to herein as oligomeric (Si, Ge or Sn substituted amino)-1,3,5-triazines. As specific examples of such may be mentioned, for example, silylated self-condensation products of melamine-formaldehyde resins, and silylated oligomers produced by the condensation of n-moles of a melamine-formaldehyde resin with one mole of an n-functional polyol, such as trimethylolpropane.

Preferred for use in the present process, however, are predominantly monomeric (Si, Ge or Sn substituted amino)-1,3,5 triazine materials which, in the above formula, are those wherein:

at least one of Z and $Z^1$ is a group represented by the formula $N(Q)_2$, and the other is selected from the group consisting of hydrogen, a hydrocarbyl, a hydrocarbyloxy, a hydrocarbylthio and a group represented by the formula —$N(Q)_2$, more preferably wherein both Z and $Z^1$ are $N(Q)_2$; and at least one Q group on each —$N(Q)_2$ group is $M(R^1)_3$. For each $M(R^1)_3$ group, preferably M is silicon and each $R^1$ is independently selected from the group consisting of substituted or unsubstituted alkyl of 1 to 20 carbon atoms, alkenyl of 3 to 20 carbon atoms, aryl of 6 to 20 atoms, aralkyl of 2 to 20 carbon atoms, arylene of 8 to 20 carbon atoms and alkoxy of 1 to 20 carbon atoms. More preferably, M is silicon and each $R^1$ is independently selected from the group consisting of an alkyl of 1 to 6 carbon atoms, most preferably methyl.

Especially preferred for use in the process of this invention is a substantially monomeric N-silylated melamine, wherein both Z and $Z^1$ are $N(Q)_2$ and at least one Q group on each —$N(Q)_2$ group is $Si(R^1)_3$. The most preferred substantially monomeric N-silylated melamine is N, N', N"-tris(trimethylsilyl) melamine.

As mentioned previously, the (Si, Ge or Sn substituted amino)-1,3,5-triazine starting materials of this invention can be prepared by the in situ reaction of an amino-1,3,5-triazine with a (Si, Ge or Sn) reactive compound. The useful amino-1,3,5-triazines are fully disclosed in the previously incorporated patents and patent applications set forth herein. Exemplary (Si, Ge or Sn) reactive compounds can be represented by the formula $W(M(R^1)_3)_n$ wherein M and $R^1$ are as previously defined, W is a leaving group and n is at least 1. Preferred leaving groups represented by W include hydrogen, halogen, halogenated acetamides and the like. Other possible leaving groups include, for example, anions of other amides, imides, carbamates, sulfonamides, sulfonimides, amines, imidates derived from imidate esters, alkyl, aryl, and aralkyl mercaptides, alkyl, aryl, and aralkyl sulfonates, perfluorosulfonates, alkyl, aryl, and aralkyl carboxylates, perfluorocarboxylates, azide, cyanide, perhaloalkyl such as trihalomethyl, alkoxy, aryloxy, aralkoxy, halogenated derivatives thereof, including perhaloalkoxy such as the trichloromethoxy derived from the reaction of silylated melamine with the phosgene equivalent di(trichloromethyl) carbonate, and the like. It is most preferred that M is silicon. Most preferred (Si, Ge or Sn) reactive compounds include for example, chlorotrimethylsilane, bis(trimethylsilyl) trifluoroacetamide, trimethylsilylimidazole, and hexamethyldisilazane.

The Acid Halides

Examples of the acid halides usable in the practice of this invention are fully set forth in previously incorporated U.S. Pat. No. 5,288,865. The preferred acid halides suitable for use in the practice of the invention include, for example, hydrocarbyl haloformates such as alkyl chloroformates and aryl chloroformates, acyl chlorides, haloalkylcarbonyl chlorides, acryloyl chlorides, carbamoyl chlorides, alkylene bis acid chlorides, phosgene and mixtures thereof.

The most preferred acid halides are methyl chloroformate, n-butyl chloroformate, n-butyl fluoroformate, phenyl chloroformate, 2-chloroethyl chloroformate, ethyl chloroformate, propyl chloroformate, isopropyl chloroformate, isobutyl chloroformate, 2-ethylhexyl chloroformate, chloroacetyl chloride, 4-chlorobutyryl chloride, acryloyl chloride, methacryloyl chloride, oxalyl chloride, ethyloxalyl chloride, benzoyl chloride, para-nitrobenzoyl chloride, acetyl chloride, stearoyl chloride, and phosgene.

A particularly preferred acid halide for use in the present invention is phosgene which is well-known to those of ordinary skill in the art as being represented by the formula ClC(O)Cl. Phosgene, as defined within the context of this invention, also includes phosgene analogs capable as serving as a phosgene source, as well as phosgene equivalents which are generally well-known to those of ordinary skill in the art. Exemplary phosgene analogs include, without limitation, diphosgene and triphosgene. Diphosgene (trichloromethyl chloroformate) and triphosgene (trichloromethyl carbonate) are represented, respectfully, by the formulas $ClC(O)CCl_3$ and $Cl_3COC(O)OCCl_3$. Triphosgene is known by those skilled in the art to be a phosgene source. See, e.g., M. J. Coghlan and B. A. Caley, "Trichloromethyl Carbonate as a Practical Phosgene Source" Tetrahedron Letters, Vol. 30, No. 16, pp. 2033–2036 (1989). Exemplary phosgene equivalents include, without limitation, N,N'-carbonyldiamidazole and dicyanocarbonyl.

The use of phosgene is most preferred in the present invention for the preparation of isocyanate-functional 1,3, 5-triazines.

The Isocyanate-Reactive Materials

As mentioned earlier, isocyanate-functional 1,3,5-triazines that are prepared by the process of this invention can be post-reacted with an isocyanate-reactive material such as an active hydrogen containing compound to form isocyanate-based 1,3,5-triazine derivatives.

A wide variety of active hydrogen containing compounds are suitable for use in forming isocyanate-based derivatives, such as carbamates, and are described in detail in the previously incorporated references. For instance, the active hydrogen containing compounds employed in this process include those known to one skilled in the art which have at least one active hydrogen moiety selected from the group consisting of carboxyl, hydroxyl, thiol, sulfonamide, amido, primary amine, secondary amine, salts thereof and mixtures thereof. As preferred examples may be mentioned alcohols, phenols, oximes, hydroxamic ethers, lactams and mixtures thereof.

As a specific preferred example, carbamate-functional 1,3,5-triazine derivatives can be formed by reacting the isocyanate-functional triazines with hydroxyl group-containing compounds. As suitable hydroxyl group-containing compounds may be mentioned, for example, straight or branched monohydric or polyhydric alkanols and alkenols having 1 to 20 carbon atoms per molecule, monohydric or polyhydric cycloalkanols and cycloalkenols having 3 to 20 carbon atoms in the molecule, and monohydric and polyhydric arylalkyls having 7 to 20 carbon atoms per molecule. Further, these alcohols may also have a substituent such as a halogen atom, a cyano group, an alkoxy group, a sulfoxide group, a sulfone group, a carbonyl group, an ester group, an ether group and an amide group. Mixtures of the above are also suitable.

Preferred of the above are the aliphatic linear, cyclic, saturated, or unsaturated alcohols having 1 to 8 carbon atoms, as well as mixtures thereof. As specific preferred examples may be mentioned methanol, ethanol, 1-propanol, 2-propanol, 1-butanol, 2-butanol, iso-butanol, tert-butanol, pentanol, hexanol, cyclohexanol, heptanol, octanol, ethylhexyl alcohol, benzyl alcohol, allyl alcohol, ethylene chlorohydrin, ethylene glycol, propylene glycol, 1,3-propanediol, 1,4-butanediol, ethoxyethanol, hydroxyethoxyethanol, 1-methoxy-2-propanol and mixtures thereof.

Phenols are also suitable as the hydroxyl group-containing compound. As specific examples may be mentioned phenol, various alkyl phenols, various alkoxy phenols, various halogenated phenols, dihydroxybenzene, 4,4-dihydroxydiphenylmethane, various bisphenols such as bisphenol-A, and hydroxynaphthalenes. As specific preferred examples may be mentioned phenol, 2-methyl phenol, 3-methyl phenol, 4-methyl phenol, 2-chlorophenol, 3-chlorophenol, 4-chlorophenol, catechol, resorcinol, hydroquinone, and mixtures thereof.

Many of the aforementioned hydroxyl group-containing compounds are well-known isocyanate blocking agents. Other well-known isocyanate blocking agents are also suitable for use herein, and include, for example, those blocking groups which deblock at relatively low temperatures, e.g., below about 125° C., such as an oxime of an aldehyde or ketone (e.g., methylethyl-ketoxime, acetone oxime and cyclohexanone oxime), lactam (e.g., caprolactam), hydroxyamic acid ester, imidazole, pyrazole, N-hydroxyimide (e.g., N-hydroxyphthalimide), dimethylamine, or other blocking groups such as recited in U.S. Pat. No. 4,444,954 the pertinent portions of which are incorporated by reference herein as if fully set forth.

For use as a crosslinking agent as described in various of the previously incorporated references, most preferred for the isocyanate-reactive compound are aliphatic alcohols and ether-alcohols having 1 to 18 carbons, such as methanol, ethanol, isopropanol, propanol, isobutanol, n-butanol, t-butanol, pentanol, hexanol, heptanol, octanol, nonanol, decanol, lauryl alcohol, 2-ethyl hexanol, alkyl alcohol, glycidol, stearyl alcohol, ethoxyethanol and 1-methoxy-2-propanol.

Process Conditions

In the process of the present invention, the (Si, Ge or Sn substituted amino)-1,3,5-triazine and the acid halide are contacted in a reaction system, under conditions such as temperature and pressure, and for length of time sufficient to produce the desired acid amide. The reaction system of the present invention is not limiting, and can be any reaction system, such as a vessel or container, which can be subject to the conditions required to obtain the desired acid amide.

The relative amounts of the (Si, Ge or Sn substituted amino) 1,3,5-triazine and acid halide employed in the process is generally in the range of about 1:1 to about 1:50 and most preferably in the range of about 1:3 to about 1:5 on an equivalent weight basis. The reactants may be mixed in varying amounts, but typically at least one equivalent of acid halide is used per equivalent of (Si, Ge or Sn substituted amino)-1,3,5 triazine. An excess of acid halide is preferably employed.

The reaction components may be contacted at any temperature and pressure conditions which will result in the formation of the acid amide. Preferably, the reaction temperature ranges from about 0° C. to about 200° C., and more preferably from about 50° C. to about 100° C. In addition, the reaction of the components is preferably conducted at a pressure in the range from about 0 psig to about 500 psig, and more preferably from about 0 psig to about 200 psig, depending upon the reaction temperature. At these temperatures and pressures, the reaction has been found to produce acid amides, including isocyanate-functional 1,3,5-triazine, in a period of time ranging from about 0.5 hours to about 20 hours.

The process may be carried out as a continuous or batch process. It may be carried out by simply admixing in any order, the (Si, Ge or Sn substituted amino)-1,3,5-triazine and the acid halide. Alternatively, as previously mentioned, the reaction may be carried out by admixing an amino 1,3,5-triazine, a Si, Ge or Sn-containing reactive compound and the acid halide to form the (Si, Ge or Sn substituted amino)-1,3,5-triazine in situ. The process can be carried out with or without solvents. If a solvent is employed, preferable solvents include nitrobenzene, chlorobenzene, dichlorobenzene, cyclic and acrylic ethers.

The reaction process is generally carried out under an atmosphere of an inert gas under substantially moisture free conditions. This minimizes the decomposition of the reactants and products by atmospheric moisture.

When the acid amide reaction product is obtained as a solution, the acid amide can be isolated by removing the volatiles under reduced pressure or by distillation. The acid amide can also be isolated by dissolving the product residue in a solvent and precipitating the acid amide by adding a solvent in which the acid amide is substantially insoluble. The acid amide product may also be purified by recrystallization, distillation or chromatographic techniques well known to those skilled in the art.

When isocyanate-functional 1,3,5-triazine is prepared by the above-described process, it may subsequently be reacted with the isocyanate-reactive material described herein and in various of the previously incorporated references. Generally, the isocyanate-functional 1,3,5-triazine and isocyanate-reactive material may be reacted at temperatures ranging from about −20° C. to about 200° C., and for varying times, depending on the isocyanate-reactive material. For most suitable blocking agents, the components are reacted at a temperatures ranging from about 20° C. to about 40° C. when adding the blocking agents. Such blocking reaction is carried out to substantial completion, generally for a time ranging from about 10 minutes to about 2 hours. The resulting isocyanate-based isocyanate-functional 1,3,5-triazines can be isolated in any desired manner, such as by filtration and distillation of the solvent.

The relative amount of isocyanate blocking agent material added to the isocyanate-functional 1,3,5-triazine is generally in the range about 3 to about 30 equivalents of isocyanate-reactive functionality per isocyanate group. Preferably, the ratio is in the range of about 3:1 to about 5:1 on such equivalent basis.

If the amount of active hydrogen containing compound added to the reaction is less than the molar equivalent of available isocyanate functionality, then the resulting 1,3,5-triazine will have a mixture of isocyanate and isocyanate-based functionality. When utilized as a "blocked isocyanate" crosslinking agent, it is preferred to add an amount of blocking agent which will react to form a fully blocked-isocyanate functional 1,3,5-triazine.

The examples which follow are intended as an illustration of certain preferred embodiments of the invention; and no limitation of the invention is implied.

EXAMPLE 1

Preparation of Tris-n-Butylcarbamoyl-1,3,5-Triazine by Phosgenation of Silylated Melamine and the Addition of n-Butanol One end of a 22 mm diameter, 285 mm long, heavy wall quartz tube was fitted with a Hastelloy C-276 end cap. The other end of the tube was flame sealed closed into a rounded bottom. A 35 mm diameter, 90 mm long water condenser was positioned concentrically onto the outside of the quartz tube approximately 40 mm from the closed end. This condenser was constructed as follows. Rubber stoppers were placed into either end of a 35 mm diameter, 90 mm long section of glass tubing. This section of glass tubing had water inlet/outlet connections near each end. Each of the rubber stoppers had been bored through the center with a single 22 mm diameter hole which the quartz tube was pushed through so that the rubber stoppers formed a seal between the outside of the quartz tube and the inside of the condenser jacket. The Hastelloy end cap had an ⅛ NPT threaded connection. This connection was attached to an electronic, recording pressure transducer and a stainless steel metering valve by means of a tee. The quartz tube was charged with N,N',N''-tris(tri-methylsilyl)melamine (100 mg). A small Teflon coated, magnetic stirring bar was placed inside the quartz tube and the tube clamped vertically in a fume hood so that the Hastelloy end cap was at the top of the quartz tube reactor. The reaction set up was attached to vacuum manifold through the metering valve. A cylinder of phosgene was also attached to the vacuum manifold. The reaction tube, vacuum manifold, and connecting tubes were evacuated. A dry ice acetone bath was placed around the lower end of the quartz reaction tube. The valve on the vacuum manifold leading to the vacuum pump was closed and the phosgene cylinder valve opened slowly. Approximately 2 mL of phosgene was condensed into the reactor.

The phosgene cylinder valve and reactor valve were closed. The vacuum manifold and connecting lines were flushed with dry nitrogen into a caustic scrubber. The dry ice acetone slurry was removed from around the end of the reaction tube and the reaction mixture allowed to warm to room temperature. The reactor was disconnected from the vacuum manifold. The reactor was pressurized to 107 psig with argon. The water flow through the condenser was started. The reaction mixture was heated to reflux by placing the lower end of the reactor in a 100° C. oil bath. The reaction mixture was stirred with a magnetic stirrer placed under the oil bath. Stirring and refluxing were continued for 17 hours. A white precipitate formed and the pressure in the reaction tube rose to 116 psig. The reaction mixture was allowed to cool to room temperature. The water flow through the condenser was stopped. The reactor valve was opened and the excess phosgene vented into a caustic scrubber. The Hastelloy cap was temporarily removed and n-butanol (2 ml) added with stirring. All of the precipitate dissolved shortly after the n-butanol addition. The reactor was opened and the reaction mixture placed in a round bottom flask. The volatile components were stripped from the reaction mixture at room temperature under high vacuum. The remaining white, solid residue was analyzed by HPLC and found to be primarily tris-n-butylcarbamoyl-1,3,5-triazine.

EXAMPLE 2

Preparation of Tris-n-Butylcarbamoyl-1,3,5-Triazine by Phosgenation of Silylated Melamine Prepared In Situ and the Addition of n-Butanol The reactor described in EXAMPLE 1 was charged with melamine (100 mg), chlorotrimethylsilane (1 mL), and nitrobenzene (2 mL). The reaction mixture was frozen in dry ice acetone slurry and the reactor evacuated. Phosgene (approximately 2 mL) was condensed into the reactor. The reactor was pressurized to 100 psig with argon. The reaction mixture was stirred magnetically and heated to reflux with a 100° C. oil bath. The reaction mixture was maintained under these conditions for 42 hours. The reactor was vented to caustic scrubber to remove the excess phosgene. The reactor was then cooled to room temperature and the excess chlorotrimethylsilane distilled from the reactor under vacuum. The Hastelloy cap was temporarily removed and n-butanol (2 mL) added. This mixture was stirred briefly. The reactor was opened and the reaction mixture filtered to remove unreacted melamine. The volatile components were removed from the filtrate giving 15 mg of solid residue. This residue was analyzed by HPLC and found to be primarily tris-n-butylcarbamoyl-1,3,5-triazine.

EXAMPLE 3

Preparation of Tris-n-Butylcarbamoyl-1,3,5-Triazine by Phosgenation of Melamine in the Presence of Bis(trimethylsilyl)trifluoroacetamide and the Addition of n-Butanol The reactor described in EXAMPLE 1 was charged with melamine (100 mg), bis(trimethylsilyl)trifluoroacetamide (1 mL), and nitrobenzene (2 mL). The reaction mixture was frozen in dry ice acetone slurry and the reactor evacuated. Phosgene (approximately 2 mL) was condensed into the reactor. The reactor was pressurized to 150 psig with argon. The reaction mixture was stirred magnetically and heated to reflux with a 115° C. oil bath. The reaction mixture was maintained under these conditions for 1.5 hours. The oil bath was lowered and the excess phosgene vented to a caustic scrubber. The reactor was placed under vacuum to remove the more volatile components of the reaction mixture. The 115° C. oil bath was raised and the reaction mixture heated with stirring for 20 min. The Hastelloy cap was temporarily removed and n-butanol (2 mL) added. The stirring and heating were continued for 15 min. The reactor was cooled, opened, and the reaction mixture filtered. The volatile components were removed under vacuum at room temperature giving 161 mg of solid residue. This residue was analyzed by HPLC and found to be primarily tris-n-butylcarbamoyl-1,3,5-triazine.

EXAMPLE 4

Preparation of Tris-n-Butylcarbamoyl-1,3,5-Triazine by Reacting Oxalyl Chloride with Silylated Melamine and Adding n-Butanol N, N',N"-tris(tri-methylsilyl)melamine (600 mg) and oxalyl chloride (5 mL) were placed in a 25 mL 14/20 round bottom flask fitted with a reflux condenser and a magnetic stirrer. This slurry was stirred at reflux for 18 hours under a nitrogen atmosphere. A sample of the reaction mixture gave a very strong isocyanate band at 2240 cm$^{-1}$ in the infrared spectrum. The volatile components of the reaction mixture were distilled from the reaction mixture at room temperature under high vacuum. The remaining solids were dissolved in n-butanol. The primary product in this solution was tri-n-butylcarbamoyl-1,3,5-triazine as determined by HPLC analysis.

EXAMPLE 5

The Preparation of Tris-n-Butylcarbamoyl-1,3,5-Triazine From Silylated Melamine and n-Butyl Chloroformate N,N',N"-tris(trimethylsilyl)melamine (600 mg) and n-butyl chloroformate (5 mL) were placed in a 25 mL 14/20 round bottom flask fitted with a reflux condenser and a magnetic stirrer. The reaction flask was placed in an oil bath at 90° C. and stirred magnetically for 18 hours under a nitrogen atmosphere. A portion of the reaction mixture was quenched with n-butanol to destroy the unreacted starting reagents and analyzed by HPLC. The HPLC trace showed the presence of tris-n-butylcarbamoyl-1,3,5-triazine.

EXAMPLE 6

The Preparation of a Mixture of Mono, Bis and Tris-n-Butylcarbamoyl-1,3,5-Triazine from Silylated Melamine and n-Butyl Fluoroformate A slurry of n-butyl chloroformate (10 g) and sodium fluoride (6 g) in anhydrous acetonitrile (40 mL) was refluxed overnight with magnetic stirring under an argon atmosphere. The reaction mixture was cooled to room temperature and the supernate was decanted from the solids. This supernate was analyzed by VPC and found to be mainly a solution of n-butyl fluoroformate in acetonitrile. This solution (2 mL) was mixed with N,N',N"-tris(trimethylsilyl)melamine (100 mg) in a small round bottom flask under an argon atmosphere. The N,N',N"-tris(trimethylsilyl)melamine dissolved giving a homogenous solution. This mixture was gently heated with a heat gun and a white precipitate immediately formed. The volatile components of the reaction mixture were removed at room temperature under high vacuum. The remaining white solids were analyzed by FAB MS and found to be a mixture of mono-, bis-, and tris-n-butylcarbamoyl-1,3,5-triazine.

Other variations and modifications of this invention will be obvious to those skilled in the art. This invention is not limited except as set forth in the following claims.

I claim:

1. A process for preparing acid amides which comprises the step of contacting:

(a) a (Si, Ge or Sn substituted amino)-1,3,5-triazine represented by the formula:

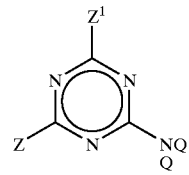

wherein
Z and $Z^1$ are independently selected from the group consisting of hydrogen, a hydrocarbyl, a hydrocarbyloxy, a hydrocarbylthio, a group represented by the formula $N(Q)_2$, and a group represented by the formula:

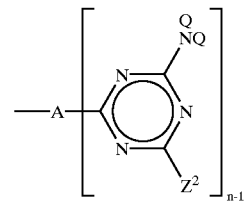

each Q is independently selected from the group consisting of hydrogen, hydrocarbyl, hydrocarbyloxy hydrocarbyl and $M(R^1)_3$, provided that at least one Q group is $M(R^1)_3$,
A is an n-functional anchor,
n is at least 2,
each $Z^2$ is independently selected from the group consisting of hydrogen, a hydrocarbyl, a hydrocarbyloxy, a hydrocarbylthio and a group represented by the formula $N(Q)_2$,
each M is independently selected from the group consisting of silicon, germanium and tin, and
each $R^1$ is independently selected from substituted or unsubstituted alkyl, alkenyl, aryl, aralkyl and alkoxy groups; and (b) an acid halide, under reaction conditions sufficient to produce a corresponding acid amide derivative.

2. The process of claim 1, wherein at least one of Z and $Z^1$ is $N(Q)_2$, and the other is selected from the group consisting of hydrogen, a hydrocarbyl, a hydrocarbyloxy, a hydrocarbylthio, and a group represented by the formula $N(Q)_2$.

3. The process of claim 2, wherein both Z and $Z^1$ are $N(Q)_2$.

4. The process of claim 3, wherein each Q is independently selected from the group consisting of hydrogen and $M(R^1)_3$.

5. The process of claim 2, wherein $Z^1$ is selected from the group consisting of hydrogen and a hydrocarbyl.

6. The process of claim 5, wherein $Z^1$ is a hydrocarbyl selected from the group consisting of an alkyl of 1 to 20 carbon atoms, an alkenyl of 3 to 20 carbon atoms, an aryl of 6 to 20 carbon atoms, and an aralkyl of 7 to 20 carbon atoms.

7. The process of claim 1, wherein M is silicon.

8. The process of claim 1, wherein each $R^1$ is independently selected from the group consisting of substituted or unsubstituted alkyl of 1 to 20 carbon atoms, alkenyl of 3 to 20 carbon atoms, aryl of 6 to 20 atoms, aralkyl of 2 to 20 carbon atoms, arylene of 8 to 20 carbon atoms and alkoxy of 1 to 20 carbon atoms.

9. The process of claim 8, wherein each $R^1$ is independently selected from the group consisting of an alkyl of 1 to 6 carbon atoms.

10. The process of claim 1, wherein $R^1$ is methyl.

11. The process of claim 1, wherein the acid halide is selected from the group consisting of hydrocarbyl haloformates, acyl chlorides, haloalkylcarbonyl chlorides, acryloyl chlorides, carbamoyl chlorides, alkylene bis acid chlorides, arylene bis acid chlorides, alkylene bis chloroformates, phosgene and mixtures thereof.

12. The process of claim 11, wherein the acid halide is selected from the group consisting of methylchloroformate, n-butyl chloroformate, n-butyl fluoroformate, phenyl chloroformate, 2-chloroethyl chloroformate, ethyl chloroformate, propyl chloroformate, isopropyl chloroformate, isobutyl chloroformate, 2-ethylhexyl chloroformate, chloroacetyl chloride, 4-chlorobutyryl chloride, acryloyl chloride, methacryloyl chloride, oxalyl chloride, ethyl oxalyl chloride, acetyl chloride, stearoyl chloride, phosgene and mixtures thereof.

13. The process of claim 1, wherein the acid halide is a hydrocarbyl haloformate.

14. The process of claims 1, wherein the acid halide is selected from the group consisting of an alkyl chloroformate and an aryl chloroformate.

15. The process of claim 1, wherein the (Si, Ge or Sn substituted amino)-1,3,5-triazine and the acid halide are contacted in an amount ranging from about 1:1 to about 1:50 on an equivalent weight basis.

16. The process of claim 1, wherein the (Si, Ge or Sn substituted amino)-1,3,5-triazine and the acid halide are contacted at a temperature ranging from about 0° C. to about 200° C. and a pressure ranging from about 0 psig to about 500 psig.

17. The process of claim 1, wherein the (Si, Ge or Sn substituted amino)-1,3,5-triazine and the acid halide are contacted under an atmosphere of an inert gas under substantially moisture free conditions.

18. A process for preparing acid amides which comprises the step of contacting:

(a) a (Si, Ge or Sn substituted amino)-1,3,5-triazine represented by the formula:

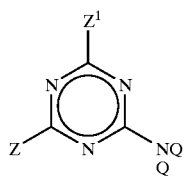

wherein

Z and $Z^1$ are independently selected from the group consisting of hydrogen, a hydrocarbyl, a hydrocarbyloxy, a hydrocarbylthio, a group represented by the formula $N(Q)_2$, and a group represented by the formula:

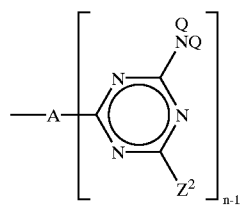

each Q is independently selected from the group consisting of hydrogen, hydrocarbyl, hydrocarbyloxy hydrocarbyl and $M(R^1)_3$, provided that at least one Q group is $M(R^1)_3$, A is an n-functional anchor, n is at least 2, each $Z^2$ is independently selected from the group consisting of hydrogen, a hydrocarbyl, a hydrocarbyloxy, a hydrocarbylthio and a group represented by the formula $N(Q)_2$ each M is independently selected from the group consisting of silicon, germanium and tin, and each $R^1$ is independently selected from substituted or unsubstituted alkyl, alkenyl, aryl, aralkyl, alkoxy groups; and (b) an acid halide selected from the group consisting of oxalyl chloride, phosgene, phosgene analogs and mixtures thereof, under reaction conditions sufficient to produce a corresponding acid amide derivative.

19. The process of claim 18, wherein at least one of Z and $Z^1$ is $N(Q)_2$, and the other is selected from the group consisting of hydrogen, a hydrocarbyl, a hydrocarbyloxy, a hydrocarbylthio, and a group represented by the formula $N(Q)_2$.

20. The process of claim 19, wherein both Z and $Z^1$ are $N(Q)_2$.

21. The process of claim 20, wherein each Q is independently selected from the group consisting of hydrogen and $M(R^1)_3$.

22. The process of claim 19, wherein $Z^1$ is selected from the group consisting of hydrogen and a hydrocarbyl.

23. The process of claim 22, wherein $Z^1$ is a hydrocarbyl selected from the group consisting of an alkyl of 1 to 20 carbon atoms, an alkenyl of 3 to 20 carbon atoms, an aryl of 6 to 20 carbon atoms, and an aralkyl of 7 to 20 carbon atoms.

24. The process of claim 21, wherein M is silicon.

25. The process of claim 18, wherein each $R^1$ is independently selected from the group consisting of substituted or unsubstituted alkyl of 1 to 20 carbon atoms, alkenyl of 3 to 20 carbon atoms, aryl of 6 to 20 atoms, aralkyl of 2 to 20 carbon atoms, arylene of 8 to 20 carbon atoms and alkoxy of 1 to 20 carbon atoms.

26. The process of claim 8, wherein each $R^1$ is independently selected from the group consisting of an alkyl of 1 to 6 carbon atoms.

27. The process of claim 10, wherein $R^1$ is methyl.

28. The process of claim 18, further comprising the step of contacting the reaction product of the (Si, Ge or Sn substituted amino)-1,3,5-triazine and the acid halide with an isocyanate-reactive material at a temperature, pressure and for a length of time sufficient to form a n isocyanate-based 1,3,5-triazine derivative.

29. The process of claim 28, wherein the isocyanate-reactive material is a hydroxyl group-containing compound.

30. The process of claim 29, wherein the isocyanate-reactive material is an alcohol having 1 to 8 carbon atoms.

31. The process of claim 18, wherein the (Si, Ge or Sn substituted amino)-1,3,5-triazine and the acid halide are contacted in an amount ranging from about 1:1 to about 1:50 on an equivalent weight basis.

32. The process of claim 18, wherein the (Si, Ge or Sn substituted amino)-1,3,5-triazine and the acid halide are contacted at a temperature ranging from about 0° C. to about 200° C. and a pressure ranging from about 0 psig to about 500 psig.

33. The process of claim 18, wherein the (Si, Ge or Sn substituted amino)-1,3,5-triazine and the acid halide are contacted under an atmosphere of an inert gas under substantially moisture free conditions.

34. The process of claim 18, wherein the (Si, Ge or Sn substituted amino)-1,3,5-triazine and the acid halide are contacted in an amount ranging from about 1:1 to about 1:50 on an equivalent weight basis, at a temperature ranging from about 0° C. to about 200° C. and a pressure ranging from about 0 psig to about 500 psig, and under an atmosphere of an inert gas under substantially moisture free conditions.

* * * * *